United States Patent
Barron et al.

(10) Patent No.: US 10,251,741 B2
(45) Date of Patent: *Apr. 9, 2019

(54) URETERAL STENT WITH DRUG-RELEASING STRUCTURE

(71) Applicant: Boston Scientific Scimed, Inc., Maple Grove, MN (US)

(72) Inventors: Heidi J. Barron, Acton, MA (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/246,632

(22) Filed: Aug. 25, 2016

(65) Prior Publication Data
US 2016/0361152 A1  Dec. 15, 2016

Related U.S. Application Data

(63) Continuation of application No. 14/164,316, filed on Jan. 27, 2014, now Pat. No. 9,445,884.

(60) Provisional application No. 61/758,464, filed on Jan. 30, 2013.

(51) Int. Cl.

| | |
|---|---|
| *A61F 2/04* | (2013.01) |
| *A61M 27/00* | (2006.01) |
| *A61K 31/00* | (2006.01) |
| *A61L 31/14* | (2006.01) |
| *A61L 31/16* | (2006.01) |
| *A61K 9/00* | (2006.01) |

(52) U.S. Cl.
CPC ............. *A61F 2/04* (2013.01); *A61K 31/00* (2013.01); *A61L 31/148* (2013.01); *A61L 31/16* (2013.01); *A61M 27/008* (2013.01); *A61F 2002/048* (2013.01); *A61F 2210/0004* (2013.01); *A61F 2220/0008* (2013.01); *A61F 2250/0067* (2013.01); *A61K 9/0036* (2013.01)

(58) Field of Classification Search
CPC ...... A61F 2/82; A61F 2/91; A61F 2/04; A61F 2/042; A61F 2002/047
See application file for complete search history.

(56) References Cited

U.S. PATENT DOCUMENTS

| | | | |
|---|---|---|---|
| 6,545,097 B2 | 4/2003 | Pinchuk et al. | |
| 2008/0021534 A1* | 1/2008 | Stratford | A61L 29/085 623/1.11 |
| 2008/0113000 A1* | 5/2008 | Hunter | A61L 27/34 424/426 |
| 2008/0292777 A1* | 11/2008 | Anderson | A61F 2/82 427/2.24 |
| 2009/0187240 A1* | 7/2009 | Clerc | A61F 2/07 623/1.17 |
| 2012/0016490 A1* | 1/2012 | Li | A61M 27/002 623/23.66 |

* cited by examiner

*Primary Examiner* — Jason-Dennis N Stewart (57) ABSTRACT

According to one aspect of the present disclosure, ureteral stents are provided that comprise an elongated stent body, at least one deployable retention structure, and at least one sleeve and/or sheet of drug-releasing material. In various embodiments, at least one sleeve and/or sheet of drug-releasing material is deployed concurrently with the deployment of at least one deployable retention structure. The ureteral stents of the present disclosure are adapted to release the urologically beneficial drug into a subject.

20 Claims, 3 Drawing Sheets

Fig. 9

URETERAL STENT WITH DRUG-RELEASING STRUCTURE

CROSS-REFERENCE TO RELATED APPLICATION

This application is a continuation of U.S. Ser. No. 14/164,316, filed Jan. 27, 2014, which claims the benefit of U.S. Ser. No. 61/758,464, filed Jan. 30, 2013 and entitled "URETERAL STENT WITH DRUG-RELEASING STRUCTURE," which is hereby incorporated by reference in its entirety.

FIELD OF THE INVENTION

The present invention relates generally to ureteral stents, and more particularly to ureteral stents which release drugs within the body of a patient.

BACKGROUND OF THE INVENTION

Ureteral stents are widely used to facilitate drainage in the upper urinary tract (e.g., from the kidney to the bladder), for example, following ureteroscopy, endourerotomies, and endopyelotomy for ureteral strictures, as well as in other instances where ureteral obstruction may occur, for example, following lithotripsy.

Figure 1:
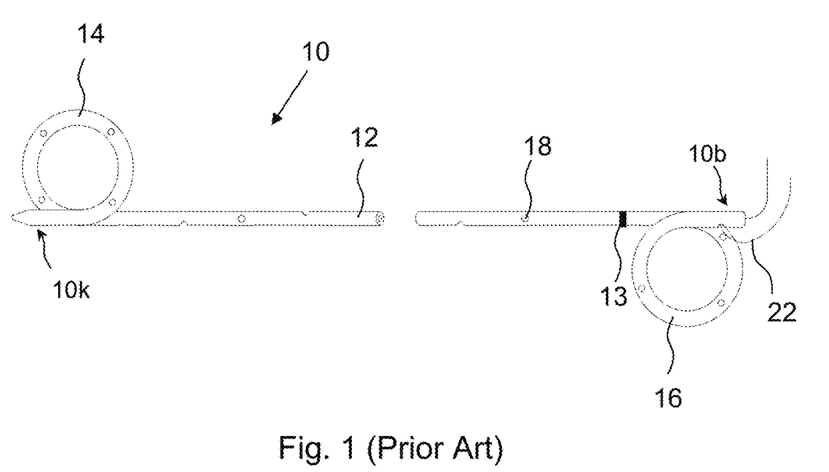
FIG. 1 is a side view of a ureteral stent, in accordance with the prior art.

A schematic diagram of a stent 10 in accordance with the prior art is schematically illustrated in FIG. 1. The stent 10 comprises an elongated stent body in the form of a tubular polymeric extrusion including a renal coil 14, bladder coil 16, and a substantially linear shaft 12 between the coils 14, 16. The stent 10 shown is further provided with the following: (a) a tapered distal tip 10k, to aid insertion, (b) multiple side ports 18 (one numbered), which are arranged in a spiral pattern along the length of the stent body to promote drainage, (c) graduation marks 13 (one illustrated), which are used for visualization by the physician to know when the appropriate length of stent has been inserted into the ureter, and (d) a Nylon suture 22, which aids in positioning and withdrawal of the stent, is provided at the proximal end 10b of the stent, as is known in that art. During placement, the ureteral stent 10 may be placed over a guide wire, through a cystoscope and advanced into position with a positioner.

Figure 2:
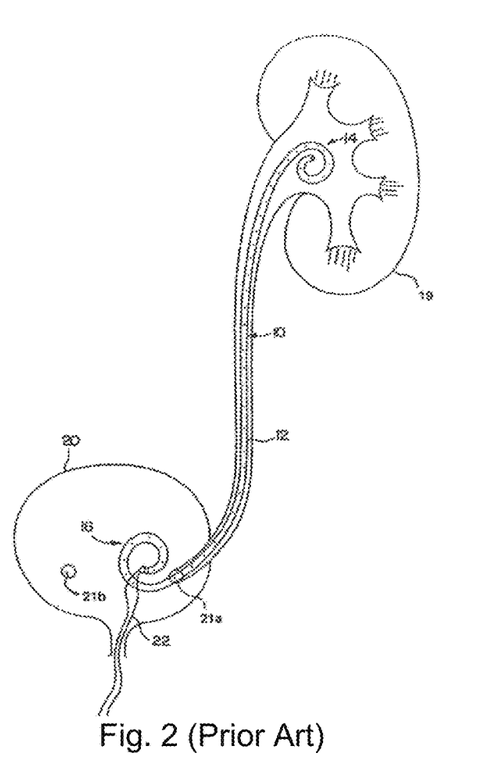
FIG. 2 shows the ureteral stent of FIG. 1 as positioned within the body.

Referring now to FIGS. 1 and 2, once the distal (kidney) end 10k of the stent is advanced into the kidney 19, the guide wire is removed, allowing the coils 14, 16 to form in the kidney 19 and bladder 20. As shown in FIG. 2, the stent 10 extends through the ureteral orifice 21a and into the bladder 20. For clarity, the ureter entering bladder 20 through the opposite ureteral orifice 21b is not shown.

Such stents, however, are commonly associated with pain and discomfort in the bladder and flank area after insertion. One way to minimize pain and discomfort is to orally administer drugs to the patient. Commonly prescribed oral drugs are opioid analgesia (e.g. Vicodin® and Percocet®), which are controlled substances and have the potential for abuse by patients.

Another way to address pain and discomfort is to release a therapeutic agent from the ureteral stent. See Pub. Nos. US 2003/0224033 to Li et al., US 2006/0264912 to McIntyre et al., US 2009/0187254 to Deal eat al., and US 2009/0248169 to Li et al.

SUMMARY OF THE INVENTION

According to one aspect of the invention, ureteral stents are provided that comprise an elongated stent body, at least one deployable retention structure, and at least one sleeve of drug-releasing material.

According to another aspect of the invention, ureteral stents are provided that comprise an elongated stent body, at least one deployable retention structure, and at least one sheet of drug-releasing material. In various embodiments, at least one sheet of drug-releasing material is deployed concurrently with the deployment of at least one deployable retention structure.

The ureteral stents of the present disclosure are adapted to release the urologically beneficial drug into the subject.

Other aspects of the invention pertain to methods of forming such stents and methods of using such stents.

These and other aspects, as well as various embodiments and advantages of the present invention will become immediately apparent to those of ordinary skill in the art upon review of the Detailed Description and any claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

According to one aspect of the present disclosure, ureteral stents are provided that comprise an elongated stent body, at least one deployable retention structure (e.g., a kidney coil, a bladder coil, or both), and at least one sleeve of drug-releasing material (also referred to herein as a "drug-releasing sleeve").

Figure 3A:
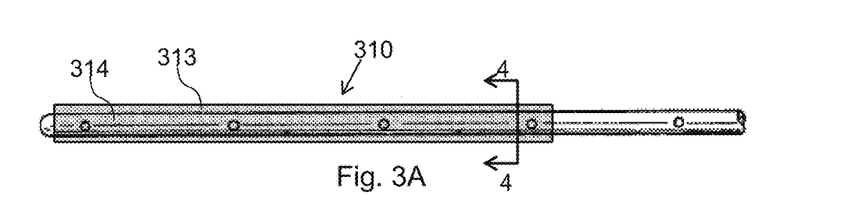
FIG. 3A is a schematic illustration of the kidney end of a ureteral stent, in accordance with an embodiment of the invention.
Figure 3B:
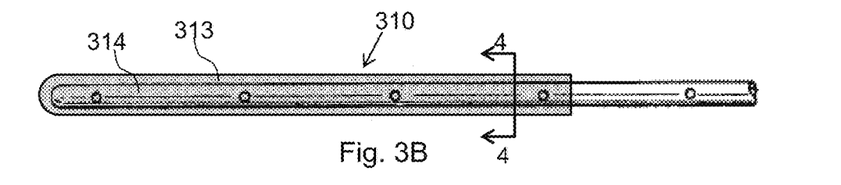
FIG. 3B is a schematic illustration of the kidney end of a ureteral stent, in accordance with another embodiment of the invention.
Figure 4:
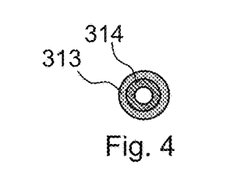
FIG. 4 is a cross-section taken along line 4-4 in FIG. 3A or FIG. 3B.

For example, FIGS. 3A and 3B are schematic illustrations of a kidney coil portion 314 of ureteral stent 310 in linear form, in accordance with two embodiments of the present disclosure. A kidney coil portion 314 may be placed in substantially linear form, for example, by placing the stent 310 over a guidewire (not shown), with the kidney coil portion 314 returning to its naturally coiled shape upon removal of the guidewire (and thus removal of the straightening force associated with the guidewire). Disposed over the kidney coil portion 314 is flexible drug-releasing sleeve 313. The drug releasing sleeve 313 may be open ended as shown in 3A or closed ended as shown in FIG. 3B (although a small hole may be formed in the sleeve of FIG. 3B to allow for the insertion of a guidewire). FIG. 4 is a cross-section taken along line 4-4 in FIG. 3A or FIG. 3B, showing the sleeve 313 disposed over the kidney coil portion 314.

The drug-releasing sleeve may be disposed over any portion of the stent or all of the stent. For example, one or more drug-releasing sleeves may be disposed over any combination of one or more of the following locations, among others: (a) disposed over a kidney coil portion of a ureteral stent (see, e.g., FIGS. 3A and 3B), (b) disposed over a bladder coil portion of a ureteral stent, and (c) disposed over the shaft portion lying between the coils. In some embodiments, one stent may have multiple drug-releasing sleeves, which may contain the same or different therapeutic agents (e.g., selected from those described below, among others).

The use of drug-releasing sleeves provides a health care professional (e.g., a urologist) with an option to select one or more drug-releasing sleeves from a number of available drug-releasing sleeves, which may differ, for example, based on one or more the following characteristics, among others: (a) the type of therapeutic agent in the sleeves, (b) the concentration of therapeutic agent in the sleeves, (c) the thickness of the sleeves and (d) the length of the sleeves. For example, in some embodiments, a drug-releasing sleeve with a first therapeutic agent may be selected for use over a kidney coil portion of a ureteral stent and a drug-releasing sleeve with a second differing therapeutic agent may be selected for use over a bladder coil portion of the ureteral stent. In some embodiments, drug-releasing sleeves are provided which are marked (e.g., labeled, color-coded or otherwise visually identifiable) to reflect the particular characteristics of the sleeve.

In some embodiments, the sleeve may be provided on the stent in the form of a layer or coating, for instance, during the manufacturing process.

The sleeve may be a solid film (which may include one or more layers), or it may be in the form of a film with a number of openings formed there in, or it may be formed from one or more filaments, for example, being in the form of a mesh, web, netting, and so forth.

Typically, the drug-releasing sleeve may have an internal diameter ranging, for example, from 1 mm to 4 mm (e.g., from 1 to 2 to 3 to 4 mm) and a length ranging, for example, from 2 to 500 mm (e.g., from 2 to 5 to 10 to 25 to 50 to 100 to 250 to 500 mm in length), among other values. Typical thicknesses of the drug-releasing sleeve may range, for example, between 50 and 200 µm (e.g., 50 to 75 to 100 to 150 to 200 µm), among other values.

In certain embodiments, the drug-releasing sleeve may be formed from an elastic material which allows the drug-releasing sleeve to be firmly secured to the ureteral stent upon expansion and contraction, a heat-shrinkable material which allows the drug-releasing sleeve to be firmly secured to the ureteral stent upon application of heat, and so forth.

According to another aspect of the present disclosure, ureteral stents are provided that comprise an elongated stent body, at least one deployable retention structure, and at least one sheet of drug-releasing material (also referred to herein as a "drug-releasing sheet"). In various embodiments, at least one sheet of drug-releasing material is deployed (e.g., furled, unfolded or otherwise spread out) concurrently with the deployment of at least one deployable retention structure.

As used herein a "sheet" of material is one whose length and width are at least 10 times greater than its thickness, for example, one whose length and width are each 10 to 25 to 50 to 100 or more times the thickness. As used herein, a sheet of material may be a solid film (which may include one or more layers), or it may be in the form of a solid film with a number of openings formed there in, or it may be formed from one or more filaments, for example, being in the form of a mesh, web, netting, and so forth.

Sheets in accordance with the present disclosure may have at least one edge that is connected to, or that is configured to be connected to, a ureteral stent (e.g., to a stent body and/or retention member) and at least one other edge that is not attached to any portion of the stent.

Figure 5:
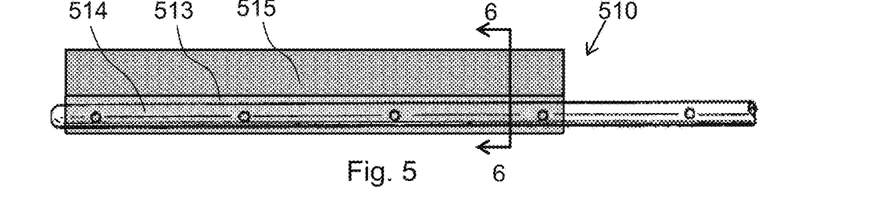
FIG. 5 is a schematic illustration of the kidney end of a ureteral stent, in accordance with another embodiment of the invention.
Figure 6:
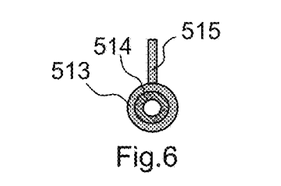
FIG. 6 is a cross-section taken along line 6-6 in FIG. 5.

For example, FIG. 5 is a schematic illustration of a kidney coil portion 514 of ureteral stent 510 in linear form, in accordance with an embodiment of the present disclosure. As noted above, the kidney coil portion 514 may be placed in substantially linear form, for example, by placing the stent 510 over a guidewire (not shown), with the kidney coil portion 514 returning to its naturally coiled shape upon removal of the guidewire. Disposed over the kidney coil portion 514 is a flexible sleeve 513, which may be a drug-releasing sleeve or which may contain no therapeutic agent. Associated with the sleeve 513 and disposed along its length is a drug-releasing sheet 515. The drug-releasing sheet 515 may be associated with the sleeve 513 by affixing an edge of the sheet 515 to the sleeve 513 using a suitable adhesive or by co-forming the sheet 515 and sleeve 513 (e.g., by extrusion or by injection molding). FIG. 6 is a cross-section taken along line 6-6 in FIG. 5, showing the sleeve 513 with attached drug-releasing sheet 515 disposed over the kidney coil portion 514. The sleeve 513 is open ended as shown in FIG. 5, but may also be closed ended as shown in FIG. 3A.

Although the drug-releasing sheet 515 is attached to the stent 510 via a sleeve 513 in FIG. 5, in other embodiments, the sheet 515 may be secured to the stent, for example, by using a suitable adhesive whereby an edge of the sheet 515 is directly attached to the stent 510, by using a snap-fit mechanism or lockey fit mechanism, or by co-forming the stent and sleeve (e.g., by extrusion or injection molding). Moreover, while a single sheet 515 is shown, multiple smaller sheets (e.g., in the form of multiple strips, tassles, etc.) may be employed.

Moreover, although the drug-releasing sheet 515 and sleeve 513 are shown attached to a kidney coil portion of a ureteral stent in FIG. 5, a drug-releasing sleeve may also be secured various other portions of the stent or to the entire stent, as noted above.

Typically, the width of the drug releasing sheets may range, for example, from 2 to 15 mm (e.g., from 2 to 5 to 10 to 15 mm), among other values, and the length of the drug releasing sheets may range, for example, from 5 to 500 mm (e.g., from 5 to 10 to 20 to 50 to 100 to 200 to 500 mm in length), respectively, among other values. Typical thicknesses of the drug releasing sheet range, for example, between 50 and 200 µm (e.g., 50 to 75 to 100 to 150 to 200 µm), among other values.

Although a portion of the drug-releasing sheet (e.g., an edge) is typically attached to a retention structure in the devices of the present disclosure, other portions of the drug-releasing sheet are freestanding, allowing the sheet to be deployed (e.g., furled, unfolded or otherwise spread out) in the body.

The drug-releasing sleeves and/or sheets described herein preferably comprise a biodisintegrable material. As used herein a "biodisintegrable" material is one that biodisintegrates (e.g., dissolves, biodegrades, bioerodes, etc.) once placed in the body. Thus, the sleeve and/or sheet of material may be, for example, soluble in urine and/or biodegraded in urine. Typically, biodisintegration of the sleeve and/or sheet material occurs over a period within the range of, for example, from 12 hours to 30 days (e.g., from 0.5 to 1 to 2 to 5 to 10 to 20 to 30 days), among other values.

In one aspect, the present disclosure provides ureteral stents that are adapted to release one or more urologically beneficial drugs in pharmaceutically effective amounts. For example, such agents may be provided in amounts effective to achieve the following benefits, among others: (a) the relief of pain and/or discomfort associated with the ureteral stent, (b) treatment of a disease or condition associated with the kidney, ureter and/or bladder, such as cancer, among others, (c) stone dissolution, (d) ureteral wall relaxation, and (e) the prevention of infection, among other benefits. As used herein, "treatment" refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects, pets and livestock.

In some aspects, drug released from a sleeve and/or sheet associated with the bladder retention structure may be different from the drug released from a sleeve and/or sheet associated with the kidney retention structure. For example, one urologically beneficial drug may be released in the kidney to address stent pain, discomfort and flank pain in the upper urinary tract, while another urologically beneficial drug may be released into the bladder to address infection and/or biofilm formation, or to treat bladder cancer.

In some aspects, multiple drugs (e.g., any combination of two or more drugs selected from drugs having analgesic activity, muscle relaxant activity, anti-spasmodic activity, anti-inflammatory activity, anti-cancer activity, anti-microbial activity, etc.) may be released from a single device component. For example, multiple drugs may be released from a sleeve and/or sheet associated with the bladder retention structure, or multiple drugs may be released from a sleeve and/or sheet associated with the kidney retention structure, or both. In a specific example, because drug released in the kidney eventually flows down the ureter and into the bladder, one or more drugs to address stent pain, discomfort and flank pain in the upper urinary tract and one or more drugs to address infection, cancer and/or biofilm formation may be released from a sleeve and/or sheet associated with the kidney retention structure.

The retention structure may take on a particular beneficial shape in vivo, for example, upon removal of a guide wire and/or emergence from a channel such as the working channel of an endoscope (e.g., due to rebound of a material having a shape memory) or upon activation by a physician. For example, in some embodiments the retention structure may have a shape memory that causes the retention element to take on a non-linear form in the body, for example, a loop, coil or corkscrew configuration, among others. In other embodiments, the retention structure may comprise a plurality of structural elements that expand radially (e.g., due to shape memory), for example, an umbrella-shaped or spheroidal configuration, among various others. Such constructions allow the ureteral stent to be held in place in the urinary tract by deployment of a retention structure in the kidney (e.g., in the renal calyx and/or renal pelvis), the bladder, or both.

As noted above, in one aspect, the present disclosure provides ureteral stents that comprise an elongated stent body, at least one deployable retention structure, and at least one sleeve and/or sheet of drug-releasing material. As will be seen from the Figures described below, in various embodiments, at least one sheet of drug-releasing material is deployed (e.g., furled, unfolded or otherwise spread out) concurrently with the deployment of at least one deployable retention structure.

Figure 7:
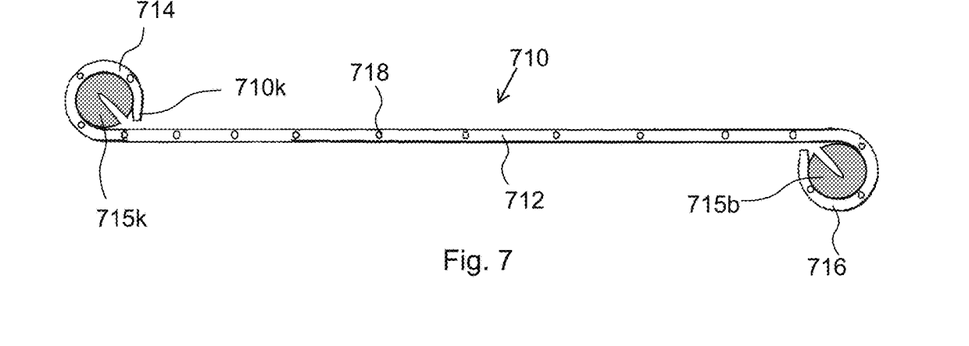
FIG. 7 is a schematic illustration of a ureteral stent that comprises deployed drug-releasing sheets in conjunction with kidney and bladder retention coils, in accordance with an embodiment of the invention.

For example, turning to FIG. 7, there is schematically illustrated therein a stent 710 in accordance with the present disclosure. The stent 710 comprises an elongated stent body in the form of a tubular polymeric extrusion including a renal coil 714, bladder coil 716, and a substantially linear shaft 712 between the coils 714, 716. The stent 720 shown is further provided with a tapered distal tip 710$k$, to aid insertion, and multiple side ports 718 (one numbered), which are arranged along the length of the stent body to promote drainage. A sheet of drug-releasing material 715$k$ is spread out within the kidney coil 714 upon formation of the kidney coil 714 in vivo. A sheet 715$k$ like that shown may be created by forming a coil (e.g., by removing a guide wire) from a kidney coil portion 514 of a ureteral stent 510 analogous to that described in conjunction with FIGS. 5 and 6, such that the drug-releasing sheet 515 like that described in conjunction with FIGS. 5 and 6 rearranges its shape to form a sheet of drug-releasing material 715$k$ like that shown in FIG. 7. A sheet of drug-releasing material 715$b$ may be likewise spread out within the bladder coil 716 upon formation of the bladder coil 716 in vivo.

Figure 8:
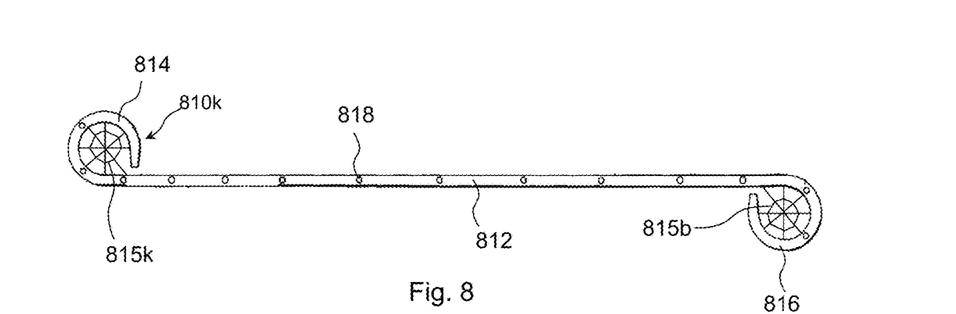
FIG. 8 is a schematic illustration of a ureteral stent that comprises deployed drug-releasing sheets in conjunction with kidney and bladder retention coils, in accordance with another embodiment of the invention.

As another example, turning to FIG. 8, a sheet of drug-releasing material 715$k$ (in the form of an elastic web) is spread out within the kidney coil 814 upon formation of the kidney coil 814 in vivo. Similarly, a sheet of drug-releasing material 815$b$ (also in the form of an elastic web) is spread out within the bladder coil 816 upon formation of the bladder coil 816 in vivo. By forming the sheets of drug-releasing material 815$k$ and 815$b$ using an elastic material (e.g., elastic filaments), the kidney coil 814 and bladder coil 816 may be straightened such that the stent can be deployed, for instance, over a guidewire (e.g., through a cystoscope).

The sheet of drug-releasing material, however, does not need to be elastic in nature. For example, in some embodiments, the sheet of drug-releasing material may not be flat (e.g., it may be wrinkled) upon deployment in the body.

While a circular coil is shown in FIGS. 7 and 8, retention structures in a variety of other shapes may be provided including oval coils, and polygonal coils, among others. The two coils may be of the same diameter or different in diameter.

Numerous other designs may be employed whereby drug-releasing sleeves and/or sheets of material may be deployed in conjunction with kidney retention structures, bladder retention structures, or both.

Figure 9:
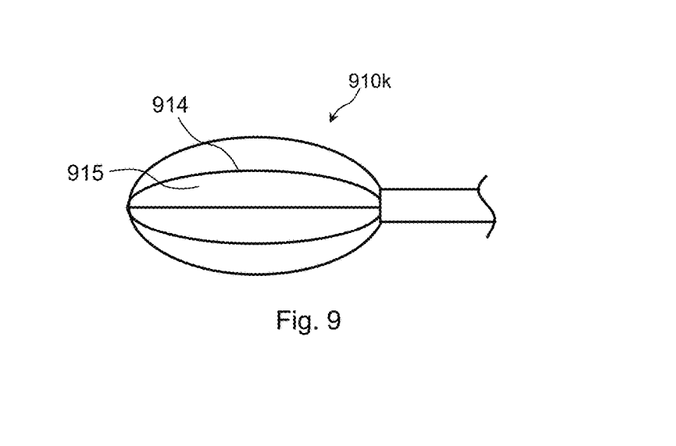
FIG. 9 is a schematic illustration of the kidney end of a ureteral stent, in accordance with an embodiment of the invention.

As one specific example, an end of a ureteral stent, for instance, a distal (kidney) end 910$k$, is schematically shown in FIG. 9 and includes a retention structure 914 that is formed from a plurality of elongated structural elements and a sheet of drug-releasing material 915 associated with the retention structure 914. The structural elements forming the retention structure 914 may be elastic materials with a shape memory (e.g., a shape memory polymer, or a shape memory metal such as nitinol, etc.) and can be compressed within a delivery tube (e.g., a cystoscope). When forced from the delivery tube at the time of delivery, the structural elements expand to form a fully deployed retention structure 914 shown in FIG. 9. While a spheroidal retention structure is shown in FIG. 9 (specifically a prolate spheroid, although oblate spheroids and spheres are also useful), retention structures in a variety of other shapes may be formed.

The sheet of drug-releasing material 915 may be elastic or inelastic in character. Where elastic, the sheet 915 may be stretched into an expanded form upon deployment of the retention structure 914. Where inelastic, the sheet 915 may be folded (analogous to fabric in an umbrella) and unfurled upon deployment of the retention structure 914 or may be flat during placement and wrinkled upon deployment.

While the retention structure 914 and drug-releasing sheet 915 shown in FIG. 9 correspond to the kidney end of a ureteral stent, an analogous structure could be employed at the bladder end of the device, or at both the kidney and bladder ends of the device.

The stent body and retention structures may be formed from a variety of metallic and non-metallic materials, with polymeric materials being preferred in certain embodiments, more preferably polymeric materials capable of being provided with a shape memory.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to the free monomers and those that are incorporated into polymers, with the distinction being clear from the context in which the term is used.

Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, for instance an initiator molecule or a linking molecule), comb configurations (e.g., configurations having a main chain and a plurality of side chains), dendritic configurations (e.g., arborescent and hyperbranched polymers), networked (e.g., crosslinked) configurations, and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers. As used herein, "block copolymers" are copolymers that contain two or more polymer blocks that differ in composition, for instance, because a constitutional unit (i.e., monomer) is found in one polymer block that is not found in another polymer block. As used herein, a "polymer block" is a grouping of constitutional units (e.g., 2 to 5 to 10 to 25 to 50 to 100 to 250 to 500 to 1000 or more units). Blocks can be branched or unbranched, and they may be networked (e.g., by crosslinking). Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution.

In embodiments like those shown in FIGS. 3A, 3B, 5, 7 and 8, where the retention structures (i.e., coils) are formed from the stent body, the stent body may be formed from material having a single composition. Alternatively, the stent body may be formed of a material of varying composition, for instance, varying from a relatively hard material for use in the kidney retention structure and a relatively soft material being used for the bladder structure, with the substantially linear (ureter) section displaying either a gradual composition change along its length or an abrupt composition change at some point along its length.

Polymers used for forming the stent body and retention structures of the present disclosure include biodisintegrable and biostable polymers, more typically biostable polymers, which may be selected, for example, from various thermoplastic polymers, elastomeric polymers, and thermoplastic-elastomeric polymers.

Polymers for use in the stent body and retention structures of the present disclosure may be selected, for example, from polycarbonates, silicone polymers, polyurethanes, poly (ether-block-amides), and alkene polymers, among others.

Polycarbonates are derived from the reaction of carbonic acid derivatives with aromatic, aliphatic, or mixed diols. They may be produced, for example, by the reaction of phosgene with a diol in the presence of an appropriate hydrogen chloride receptor or by a melt transesterification reaction between a diol and a carbonate ester. Polycarbonates can be made from a wide variety of starting materials. For example, a common polycarbonate, bisphenol A polycarbonate, is a polycarbonate made by reacting bisphenol A with phosgene by condensation. For further information, see, e.g., U.S. Pat. No. 5,580,924 and the references cited therein.

Silicone polymers (also referred to as polysiloxanes) are polymers comprising one or more types of siloxane units, where $R_1$ and $R_2$ can be the same or different and may be selected from linear, branched and cyclic alkyl groups, aromatic groups and alky-aromatic groups, for example, having from 1 to 10 carbon atoms, and having 5 or more, typically 10 to 25 to 50 to 100 to 250 to 500 to 1000 or more siloxane units. Examples include polydimethylsiloxane, polydiethyl siloxane, polymethylethyl siloxane, polymethylphenylsiloxane, and polydiphenylsiloxane, among many others. Such polymers are commonly crosslinked.

In general, polyurethanes are a family of polymers that are synthesized from polyfunctional isocyanates (e.g., diisocyanates, including both aliphatic and aromatic diisocyanates) and polyols (also, referred to as macroglycols, e.g., macrodiols). Commonly employed macroglycols include polyester glycols, polyether glycols, polycarbonate glycols and polyolefin glycols. Typically, aliphatic or aromatic diols are also employed as chain extenders, for example, to impart the useful physical properties. Examples of diol chain extenders include butane diol, pentane diol, hexane diol, heptane diol, benzene dimethanol, hydraquinone diethanol and ethylene glycol. Polyurethanes are commonly classified based on the type of macroglycol employed, with those containing polyester glycols being referred to as polyester polyurethanes, those containing polyether glycols being referred to as polyether polyurethanes, those containing polycarbonate glycols being referred to as polycarbonate polyurethanes and those containing polyolefin glycols being referred to as polyolefin polyurethanes Polyurethanes are also commonly designated as aromatic or aliphatic on the basis of the chemical nature of the diisocyanate component in their formulation. For example, U.S. Patent App. No. 2004/0131863 to Belliveau et al. describes aliphatic polycarbonate polyurethanes which are the reaction products of (a) a hydroxyl terminated polycarbonate, (b) an aliphatic diisocyanate and (c) a lower aliphatic chain extender. Hydroxyl terminated polycarbonate polyol may be prepared by reacting a glycol with a carbonate, as disclosed in U.S. Pat. No. 4,131,731. Suitable aliphatic diisocyanates include hexamethylene diisocyanate (HDI), isophorone diisocyanate (IPDI), trimethyl hexamethylene diisocyanate (TMHDI), dicyclohexyl methane diisocyanate (HMDI), and dimer acid diisocyanate (DDI), with HMDI said to be preferred. Suitable chain extenders include lower aliphatic glycols having from about 2 to about 10 carbon atoms, such as, for instance ethylene glycol, diethylene glycol, propylene glycol, dipropylene glycol, 1,4-butanediol, 1,6-hexanediol, 1,3-butanediol, 1,5-pentanediol, 1,4-cyclohexanedimethanol hydroquinone di(hydroxyethyl) ether, neopentyglycol, and the like, with 1,4-butanediol said to be preferred.

Another group of polymers are block copolymers comprising polyether blocks (i.e., polymer blocks containing multiple C—O—C linkages) and polyamide blocks (i.e., polymer blocks containing multiple —NH—CO— linkages), sometimes referred to as polyether-block-amides or poly(ether-b-amides). A few specific examples of polyether blocks include homopolymeric and copolymeric blocks of the formulas (a) —[$R_1$—O—]$_n$— or (b) —[$R_1$—O—$R_2$—O]$_n$—, where $R_1$ and $R_2$ can be the same or different and may be selected from linear, branched and cyclic alkyl groups, aromatic groups and alky-aromatic groups, for example, having from 1 to 10 carbon atoms (more typically linear or branched alkyl groups having from 1 to 6 carbons) and where n is an integer of 5 or more, typically 10 to 25 to 50 to 100 to 250 to 500 to 1000 or more. Polyethers may be formed, for example, from ring opening addition polymerization of cyclic ethers, such as ethylene oxide, where $R_1$=$R_2$=dimethylene (i.e., [—($CH_2$)$_2$—O—]$_n$), which is commonly referred to as polyethylene glycol or as polyethylene oxide), trimethylene oxide, where $R_1$=$R_2$=trimethylene (i.e., [—($CH_2$)$_3$—O—]$_n$), propylene oxide, where $R_1$=$R_2$=methyl substituted dimethylene (i.e., [—$CH_2$$CH_2$($CH_3$)—O—]$_n$, referred to as polypropylene glycol or polypropylene oxide), and tetrahydrofuran, where $R_1$=$R_2$=tetramethylene (i.e., —[($CH_2$)$_4$—O]—$_n$, which is referred to as polytetramethylene glycol, polytetramethylene oxide (PTMO), or terathane). Examples of polyamide blocks, which may be provided, for example, as homopolymeric or copolymeric blocks, include polyamides of the formula —[$R_3$—NH—CO]$_m$— or —[NH—$R_3$—NH—CO—$R_4$—CO]$_m$—, where $R_3$ and $R_4$ can be the same or different and may be selected from linear, branched and cyclic alkyl groups, aromatic groups and alky-aromatic groups, for example, of 1 to 20 carbon atoms (more typically linear or branched alkyl groups having from 1 to 15 carbons, such as methyl, ethyl, propyl, isopropyl, and so forth) and where m is an integer of 5 or more, typically 10 to 25 to 50 to 100 to 250 to 500 to 1000 or more. Specific examples include nylons, such as nylon 6, nylon 4/6, nylon 6/6, nylon 6/10, nylon 6/12, nylon 11 and nylon 12. A specific example of a polyether-polyamide block copolymer is poly(tetramethylene oxide)-b-polyamide-12 block copolymer, available from Elf Atochem as PEBAX.

Further polymers include polyalkene homopolymers and copolymers with themselves and with various other monomers including those selected from vinyl aromatic monomers such as styrene, acrylic acid, methacrylic acid, and vinyl acetate. Examples of alkene monomers include ethylene, propylene, isobutylene, 1-butene, 1-pentene, 4-methyl-1-pentene, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene, among others. Specific examples of alkene copolymers include, poly(ethylene-co-vinyl acetate) (EVA), poly(ethylene-co-methacrylic acid), poly(ethylene-co-acrylic acid), and poly(isobutylene-co-styrene), among many others.

Poly(isobutylene-co-styrene) copolymers include poly (styrene-b-isobutylene-b-styrene) triblock copolymers (SIBS), which are described in U.S. Pat. No. 6,545,097 to Pinchuk et al. SIBS is a thermoplastic elastomer.

Among EVA copolymers are included random and other copolymers having a vinyl acetate weight percent ratio of from about 0.5% to 1% to 2% to 5% to 15% to 20% to 30% to 40% or more. In general, the higher the vinyl acetate content, the lower the stiffness and Durometer of the EVA.

For example, EVA having a high vinyl acetate content (e.g., 25 to 35 wt % or more) and decreased stiffness may be employed in the portion of the stent occupying the bladder for increased comfort, while EVA having a low vinyl acetate content (e.g., 10 to 20 wt % or less) and increased stiffness may be employed in the portion occupying the kidney for good retention character. The portion occupying the ureter may be of high vinyl acetate content, low vinyl acetate content or intermediate vinyl acetate content (e.g., 20 to 25 wt %); or the portion occupying the ureter gradually or abruptly transition from the high vinyl acetate content of the bladder portion to the low vinyl acetate content of the kidney portion.

As previously noted, materials for forming the drug-releasing sleeves and/or sheets of the present disclosure may be elastic or inelastic in character. Materials for forming the drug-releasing sleeves and/or sheets of the present disclosure may be inorganic or organic in character. Materials for forming the drug-releasing sleeves and/or sheets of the present disclosure may be biostable or biodisintegrable in character.

In various embodiments, the drug-releasing sleeves and/or sheets are biodisintegrable and organic in character, for example, comprising a biodisintegrable small molecule (non-polymeric) material such as a sugar (e.g., sucrose, lactose, etc.), fatty acid, or fatty acid ester, a biodisintegrable biopolymer such as a polysaccharide, polypeptide or protein (e.g., alginate, chitosan, starch, gelatin, heparin, albumin, hyaluronic acid, etc.), or a biodisintegrable synthetic polymer.

Examples of biodisintegrable synthetic polymers include, for example, soluble synthetic polymers (e.g., low molecular EVA, etc.) and biodegradable synthetic polymers which may be selected from suitable members of the following, among others: (a) polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly (trimethylene carbonate), poly(lactide-co-glycolide), poly (lactide-co-delta-valerolactone), poly(lactide-co-epsilon-caprolactone), poly(L-lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy) propane-co-sebacic acid], and poly(sebacic acid-co-fumaric acid), among others (b) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others; and (c) amino acid based homopolymers and copolymers including tyrosine-based polyarylates (e.g., copolymers of a diphenol and a diacid linked by ester bonds, with diphenols selected, for instance, from ethyl, butyl, hexyl, octyl and benzyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and benzyl esters of desaminotyrosyl-tyrosine, among others), and leucine and lysine-based polyester-amides In certain embodiments, a polymer that is both elastic and biodisintegrable is employed. Elastic biodisintegrable polymers include the following, among others: biodisintegrable block copolymers comprising biodegradable polyesters, such as block copolymers comprising polycaprolactone (PCL) and poly-L-lactic acid (PLLA) blocks and block copolymers comprising 1,3-trimethylene carbonate (PTMC) and poly-L-lactic acid (PLLA) blocks; biodisintegrable block copolymers comprising biodegradable polyesters and polyethers such as block copolymers comprising polyethylene oxide (PEO) and poly-L-lactic acid (PLLA) blocks; biodisintegrable copolymers comprising polyacids and polyols including biodisintegrable polymers comprising citric acid such as poly(1,8-octanediol-co-citric acid) and poly(1, 8-octanediol-co-malic acid-co-citric acid) and biodisintegrable polymers comprising sebacic acid such as poly(xylitol sebacate); and biodisintegrable polyurethanes including poly(ester-urethanes) such as poly(E-caprolactone-co-lactide) polyurethanes and poly(ether-ester-urethanes) such poly(E-caprolactone-co-lactide-co-ethylene oxide) polyurethanes.

In certain embodiments a polymer that is both heat shrinkable and biodisintegrable is employed.

A variety of urologically beneficial drugs may be released from the drug-releasing sleeves and/or sheets of the present disclosure.

As used herein, a "urologically beneficial drug" is an agent that is sufficiently safe and effective for use in humans or animals when released from an implantable or insertable urological device, in particular, a ureteral stent. Urologically beneficial drugs include agents that benefit the urinary tract (e.g., stone dissolution agents, ureteral wall relaxation agents, etc.) and agents that reduce side effects associated with ureteral stents, including pain or discomfort and infection, among other side effects.

In some embodiments, urologically beneficial drugs for use in the present disclosure have one or more of the following, among others: muscle relaxant activity (e.g., they have musculotropic relaxant properties, smooth muscle relaxant properties, etc.), anti-spasmodic activity, anti-inflammatory activity, analgesic activity, anti-cancer activity and anti-microbial activity.

Urologically beneficial drugs for use in the present disclosure may be selected, for example, from one or more suitable members of the following, among others: alpha-adrenergic blockers, calcium channel blockers, beta-adrenergic agonists, bronchodilators (e.g., for muscle relaxant properties), nitric oxide donors, nitric oxide releasing compounds, prostaglandins, corticosteroids, narcotic analgesic agents, non-narcotic analgesic agents, local anesthetic agents, antiproliferative agents and antineoplastic agents, among others, as well as combinations thereof.

Examples of alpha-adrenergic blockers for use in the present disclosure may be selected from suitable members of the following: alfuzosin, amosulalol, arotinilol, dapiprazole, doxazosin, ergoloid mesylates, fenspiride, idazoxan, indoramin, labetalol, manotepil, naftopidil, nicergoline, prazosin, tamsulosin, terazosin, tolazoline, trimazosin, and yohimbine, among others, as well as combinations and pharmaceutically acceptable salts, esters and other derivatives of the same. Of these, tamsulosin, alfuzosin, doxazosin, prazosin, tamsulosin and terazosin are alpha-1-adrenergic blockers, of which tamsulosin and alfuzosin are selective alpha-1-adrenergic blockers.

Examples of calcium channel blockers for use in the present disclosure may be selected from suitable members of the following: arylalkylamines (including phenylalkylamines) such as verapamil, gallopamil, bepridil, clentiazen, fendiline, mibefradil, prenylamine, semotiadil, and terodiline, benzothiazepines such as diltiazem; dihydropyridine derivatives (including 1,4-dihydropyridine derivatives) such as amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine and nitrendipine, piperazine derivatives such as cinnarizine, dotarizine, flunarizine, lidoflazine and lomerizine, calcium channel blockers such as bencyclane, etafenone, fantofarone, monatepil and perhexiline, among other calcium channel blockers, as well as combinations and pharmaceutically acceptable salts, esters and other derivatives of the same.

Examples of beta-adrenergic agonists for use in the present disclosure may be selected from suitable members of the following: albuterol, bambuterol, bitolterol, carbuterol, clenbuterol, clorprenaline, denopamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, prenalterol, procaterol, protokylol, reproterol, rimiterol, ritodrine, salmerterol, soterenol, terbutaline, tretoquinol, tulobuterol and xamoterol, among others, as well as combinations and pharmaceutically acceptable salts, esters and other derivatives of the same.

Examples of bronchodilators for use in the present disclosure may be selected from suitable members of the following: (a) ephedrine derivatives such as albuterol, bambuterol, bitolterol, carbuterol, clenbuterol, clorprenaline, dioxethedrine, ephedrine, epinephrine, eprozinol, etafedrine, ethylnorepinephrine, fenoterol, formoterol, hexoprenaline, isoetharine, isoproterenol, mabuterol, metaproterenol, n-methylephedrine, pirbuterol, procaterol, protokylol, reproterol, rimiterol, salmeterol, soterenol, terbutaline and tulobuterol, (b) quaternary ammonium compounds such as bevonium methyl sulfate, flutropium bromide, ipratropium bromide, oxitropium bromide and tiotropium bromide, (c) xanthine derivatives such as acefylline, acefylline piperazine, ambuphylline, aminophylline, bamifylline, choline theophyllinate, doxofylline, dyphylline, etamiphyllin, etofylline, guaithylline, proxyphylline, theobromine, 1-theobromineacetic acid and theophylline, and (d) other bronchodilators such as fenspiride, medibazine, methoxyphenanime and tretoquinol, among others, as well as combinations and pharmaceutically acceptable salts, esters and other derivatives of the forgoing.

Examples of nitric oxide donors/releasing molecules for use in the present disclosure may be selected from suitable members of the following: inorganic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, among others, as well as pharmaceutically acceptable salts, esters and other derivatives of the same, and combinations of the foregoing.

Examples of prostaglandins and analogs thereof for use in the present disclosure may be selected from suitable members of the following: prostaglandins such as PGE1 and PGI2 and prostacyclin analogs such as ciprostene, epoprostenol, carbacyclin, iloprost and beraprost, among others, as well as pharmaceutically acceptable salts, esters and other derivatives of the same, and combinations of the foregoing.

Examples of corticosteroids for use in the present disclosure may be selected from suitable members of the following: betamethasone, cortisone, dexamethasone, deflazacort, hydrocortisone, methylprednisolone, prednisolone, prednisone and triamcinolone, among others, as well as combinations and pharmaceutically acceptable salts, esters and other derivatives of the same.

Examples of narcotic analgesic agents for use in the present disclosure may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present disclosure may be selected from suitable members of the following: analgesic agents such as acetaminophen, and non-steroidal anti-inflammatory drugs such as aspirin, diflunisal, salsalate, ibuprofen, ketoprofen, naproxen indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present disclosure may be selected from suitable members of the following: benzocaine, cocaine, lidocaine, mepivacaine, and novacaine, among others, as well as combinations and pharmaceutically acceptable salts, esters and other derivatives of the same.

Examples of antiproliferative/antineoplastic agents for use in the present disclosure may be selected from suitable members of the following: antimetabolites such as purine analogs (e.g., 6-mercaptopurine or cladribine, which is a chlorinated purine nucleoside analog, etc.), pyrimidine analogs (e.g., cytarabine, 5-fluorouracil, etc.) and methotrexate, nitrogen mustards, alkyl sulfonates, ethylenimines, antibiotics (e.g., daunorubicin, doxorubicin, etc.), nitrosoureas, cisplatin, agents affecting microtubule dynamics (e.g., vinblastine, vincristine, colchicine, Epo D, paclitaxel, epothilone, etc.), caspase activators, proteasome inhibitors, angiogenesis inhibitors (e.g., endostatin, angiostatin, squalamine, etc.), olimus family drugs (e.g., sirolimus, everolimus, tacrolimus, zotarolimus, etc.), cerivastatin, flavopiridol and suramin, among others, as well as combinations and pharmaceutically acceptable salts, esters and other derivatives of the same.

Examples of antimicrobial agents for use in the present disclosure may be selected, for example, from triclosan, chlorhexidine, nitrofurazone, benzalkonium chlorides, silver salts, silver particles, metallic silver and antibiotics, such as rifampin, gentamicin and minocycline, and combinations thereof, among others.

Urologically beneficial drugs may be may be associated with the drug releasing sleeves and/or sheets in various ways, including the following, among others: (a) loaded in the interior (bulk) of the sleeve and/or sheet material, (b) bound to the surface of the sleeve and/or sheet material by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating that covers all or a portion of the sleeve and/or sheet material, (d) loaded in surface features (e.g., depressions) in the sleeve and/or sheet material, and (e) combinations of the forgoing.

Drug-releasing sleeves and/or sheets in accordance with the present disclosure may contain a wide range of urologically beneficial drug loadings, with the effective amount being readily determined by those of ordinary skill in the art. For example, the amount of urologically beneficial drug(s) associated with the drug-releasing sleeves and/or sheets may range, for example, from than 1 wt % or less to 2 wt % to 5 wt % to 10 wt % to 25 wt % to 50 wt % or more.

The release of the one or more urologically beneficial drugs from the drug-releasing sleeves and/or sheets will be affected by a number of variables. For example, for a given polymeric matrix material, the release profile of the urologically beneficial drug will depend, for example, upon the geometry of the drug-releasing sleeve and/or sheet (e.g., thickness, surface, area, etc.), upon the particular urologically beneficial drug(s) selected, upon the particular polymer (s) selected, and upon the relative amount of drug and matrix material, among other factors.

Ureteral stents in accordance with the present disclosure may also contain agents in addition to urologically beneficial agents. For example, imaging agents may be associated with one or more of the stent shaft, the retention structure(s) and the drug-eluting sleeve(s) and/or sheet(s).

For example, x-ray based fluoroscopy is a diagnostic imaging technique that allows real-time patient monitoring of motion within a patient. To be fluoroscopically visible, devices and/or compositions are typically rendered more absorptive of x-rays than the surrounding tissue (e.g., radiopaque materials). In various embodiments of the present disclosure, this is accomplished by the use of contrast agents. Examples of contrast agents for use in connection with x-ray fluoroscopy include metals, metal salts and oxides (particularly bismuth salts and oxides), and iodinated compounds, among others. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others.

Ultrasound uses high frequency sound waves to create an image of living tissue. A sound signal is sent out, and the reflected ultrasonic energy, or "echoes," are used to create the image. Ultrasound imaging contrast agents are materials that enhance the image produced by ultrasound equipment. Ultrasonic imaging contrast agents can be, for example, echogenic (i.e., materials that result in an increase in the reflected ultrasonic energy) or echolucent (i.e., materials that result in a decrease in the reflected ultrasonic energy). Suitable ultrasonic imaging contrast agents for use in connection with the present disclosure include solid particles ranging from about 0.01 to 50 microns in largest dimension (e.g., the diameter, where spherical particles are utilized), more typically about 0.5 to 20 microns. Both inorganic and organic particles can be used. Examples include microparticles/microspheres of calcium carbonate, hydroxyapatite, silica, poly(lactic acid), and poly(glycolic acid), among others. Microbubbles can also be used as ultrasonic imaging contrast agents, as is known in the imaging art.

Magnetic resonance imaging (MRI) produces images by differentiating detectable magnetic species in the portion of the body being imaged. In the case of $^1$H MRI, the detectable species are protons (hydrogen nuclei). In order to enhance the differentiation of detectable species in the area of interest from those in the surrounding environment, imaging contrast agents are often employed. These agents alter the magnetic environment of the detectable protons in the area of interest relative to that of protons in the surrounding environment and thereby allow for enhanced contrast and better images of the area of interest. For contrast-enhanced MRI, it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MRI contrast agents. Chelation of the gadolinium or other paramagnetic ion is believed to reduce the toxicity of the paramagnetic metal by rendering it more biocompatible, and can assist in localizing the distribution of the contrast agent to the area of interest. Further information can be found, for example, in U.S. Patent Application No. 2003/0100830 entitled "Implantable or insertable medical devices visible under magnetic resonance imaging."

In some embodiments, kits are provided in accordance with the present disclosure. Such kits may comprise, for example, two or more of the following: (a) a ureteral stent, (b) a guidewire, (c) one or more drug-releasing sleeves which can be applied to the stent and (d) one or more drug-releasing sheets which can be applied to the stent. The kits may also include packaging and information as required by a governmental regulatory agency that regulates pharmaceuticals and/or medical devices. The components of the kits may be provided in a sterile package for convenient use by a health care professional.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A ureteral stent, comprising: an elongated stent body, a deployable retention structure, a sleeve of drug-releasing material disposed over at least a portion of the deployable retention structure, and less than the entire elongated stent body, and an elastic sheet of drug-releasing material attached to the sleeve of drug-releasing material.

2. The ureteral stent of claim 1, wherein the sleeve releases one or more drugs selected from the group consisting of an alpha-adrenergic blocker, a calcium channel blocker, a beta-adrenergic agonist, a bronchodilator, a nitric oxide donor, a nitric oxide releasing compound, a prostaglandin, a corticosteroid, a narcotic analgesic agent, a non-narcotic analgesic agent, a local anesthetic agent, an antiproliferative agent and an antineoplastic agent.

3. The ureteral stent of claim 1, wherein the sleeve is a heat shrinkable sleeve.

4. The ureteral stent of claim 1, wherein the sleeve ranges from 1 to 4 mm in inner diameter, from 2 to 500 mm in length and from 50 to 200 micrometers in thickness.

5. The ureteral stent of claim 1, wherein the sheet is a biodisintegrable sheet.

6. The ureteral stent of claim 1, wherein the sheet ranges from 2 to 20 mm in width, from 2 to 500 mm in length and from 50 to 200 micrometers in thickness.

7. The ureteral stent of claim 1, wherein the retention structure is in the form of a coil or a loop and wherein the sheet of drug-releasing material spans a majority of the coil or loop area upon deployment of the retention structure.

8. The ureteral stent of claim 1, wherein the retention structure comprises a kidney retention structure.

9. The ureteral stent of claim 8, wherein the retention structure is adapted to be reduced to a profile that is sufficiently small during deployment to allow the retention structure to be delivered to the kidney.

10. The ureteral stent of claim 1, wherein the stent body and deployable retention structure comprise a biostable polymer.

11. A ureteral stent comprising:
an elongated stent body;
a deployable kidney retention structure;
a deployable bladder retention structure;
a first sleeve of drug-releasing material disposed over at least a portion of the deployable kidney retention structure, and less than the entire elongated stent body;
a second sleeve of drug-releasing material disposed over at least a portion of the deployable bladder retention structure, and less than the entire elongated stent body;
a first elastic sheet of drug-releasing material attached to the first sleeve of drug-releasing material; and
a second elastic sheet of drug-releasing material attached to the second sleeve of drug-releasing material.

12. The ureteral stent of claim 11, wherein the first sleeve of drug-releasing material and the second sleeve of drug-releasing material release the same drug.

13. The ureteral stent of claim 11, wherein the first sleeve of drug-releasing material and the second sleeve of drug-releasing material release different drugs.

14. The ureteral stent of claim 11, wherein the first and second sleeves are heat shrinkable.

15. The ureteral stent of claim 11, wherein the first and second sleeves range from 1 to 4 mm in inner diameter, from 2 to 500 mm in length and from 50 to 200 micrometers in thickness.

16. The ureteral stent of claim 11, wherein the first and second sheets are biodisintegrable.

17. A kit comprising a) a ureteral stent comprising an elongated stent body and a deployable retention structure, b) a sleeve of drug-releasing material disposed over at least a portion of the deployable retention structure, and less than the entire elongated stent body, c) an elastic sheet of drug-releasing material attached to the sleeve of drug-releasing material and d) a delivery device.

18. The ureteral stent of claim 1, wherein the elastic sheet releases one or more drugs selected from the group consisting of an alpha-adrenergic blocker, a calcium channel blocker, a beta-adrenergic agonist, a bronchodilator, a nitric oxide donor, a nitric oxide releasing compound, a prostaglandin, a corticosteroid, a narcotic analgesic agent, a non-narcotic analgesic agent, a local anesthetic agent, an antiproliferative agent and an antineoplastic agent.

19. The ureteral stent of claim 11, wherein the first elastic sheet of drug-releasing material and the second elastic sheet of drug-releasing material release the same drug.

20. The ureteral stent of claim 11, wherein the first elastic sheet of drug-releasing material and the second elastic sheet of drug-releasing material release different drugs.

* * * * *